United States Patent [19]

Fabinski

[11] Patent Number: 4,700,073
[45] Date of Patent: Oct. 13, 1987

[54] PHOTOMETER

[75] Inventor: Walter Fabinski, Kriftel, Fed. Rep. of Germany

[73] Assignee: Hartmann & Braun AG, Frankfurt am Main, Fed. Rep. of Germany

[21] Appl. No.: 836,102

[22] Filed: Mar. 4, 1986

[30] Foreign Application Priority Data

Mar. 4, 1985 [DE] Fed. Rep. of Germany ....... 3507572

[51] Int. Cl.⁴ .............................................. G01J 1/00
[52] U.S. Cl. .................................... 250/343; 250/344; 250/349
[58] Field of Search ................ 250/343, 338 GA, 344, 250/347, 348, 349, 351, 353; 356/437, 438

[56] References Cited

U.S. PATENT DOCUMENTS

| 4,027,972 | 6/1977 | Davies | 250/343 |
| 4,425,503 | 1/1984 | Watkins et al. | 250/338 GA |
| 4,491,730 | 1/1985 | Pedersen | 250/343 |
| 4,605,313 | 8/1986 | Kebabian | 250/343 |

Primary Examiner—Janice A. Howell
Attorney, Agent, or Firm—Ralf H. Siegemund

[57] ABSTRACT

An infrared photometer having a measuring cuvette with entrance and exit windows and an output detector preferably made of polyvinylidenfluoride; a second infrared detector definitely made of polyvinylidenfluoride, being partially transmissive is disposed in front of the entrance window of the cuvette, and a selecting cuvette is insertible in front of this second detector.

5 Claims, 4 Drawing Figures

PHOTOMETER

BACKGROUND OF THE INVENTION

The present invention relates to a photometer of the variety wherein modulated infrared radiation passes through a container, vessel, cuvette or the like and the exiting radiation is duly detected and the detection result is processed.

A variety of photometers are known and they serve primarily for purposes of quantitatively ascertaining the particular proportion of a particular gas within a host or carrier gas. Photometers using infrared radiation are constructed in order to operate under the principle of dispersion but other varieties are known which do not function or operate in the dispersive mode. Generally speaking reliable and troublefree operation is guaranteed if in addition to the measured value continuously a reference value or signal is provided or derived and these quantities are then brought into relation to each other.

A typical example is the infrared gas analizer URAS 2 T traded under this designation by the assignee corporation and described in a flier 20-1.12 of Hartmann & Braun AG published May 1983. This analyzer uses infrared radiation emanating from a source wherein the radiation is modulated by means of a diaphragm wheel. The modulated radiation is passed through a biparted cuvette or measuring chamber to be received by the chambers of a biparted detector. Such a device is operable under utilization of an intermittent operation of the radiation source which intermittency is the equivalent of the modulation; a diaphragm wheel is not needed in this case.

DESCRIPTION OF THE INVENTION

It is an object of the invention to provide a new and improved infrared photometer using a cuvette and an external detector; the cuvette being passed through by measuring gas and is traversed by infrared radiation whereby, however, a biparted cuvette is not used for purposes of generating a measuring beam.

In accordance with the preferred embodiment of the invention it is suggested that upstream from the cuvette an input detector of polyvinylidenfluoride is arranged in order to generate a reference signal; the input side detector being permeable or transmissive, at least in parts, to infrared radiation. At the output side the usual detector is provided. However, in furtherance of the invention it is suggested that the output detector is likewise made of polyvinylidenfluoride.

Constructing an input radiation detector and an output radiation detector in this fashion has the advantage that they can be dimensioned very large so that in fact they cover the entire aperture (in an optical sense) as provided by the measuring gas containing cuvette. Generally speaking a photometer using a modulated infrared radiation is a reliable instrument in the general sense. This reliability is not deteriorated by the direct detection of such modulated radiation. Care has to be taken that the input detector and receiver does not receive too much energy as that may lead to undue heating. Therefore upstream i.e. in front of the input receiver and detector one should provide a filter, preferably an interference filter which limits the spectrum of the infrared radiation being used to a particular band. This offers the additional advantage that certain selectivity characteristics can be introduced, bearing in mind that the absorption of many gases in the infrared radiation band is often limited to certain narrow frequencies.

Generally speaking the input receiver or detector furnishes a reference signal and the output receiver or detector furnishes the measuring signal. The relationship between reference and measuring signal is adjustable and predeterminable generally through increasing or decreasing the absorption capacity of input and/or output receiver. A simple means for attaining this objective is the providing of a black core across a portion of one or the other or both of the receivers.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

Proceeding to the detailed description of the drawings, FIG. 1 illustrates a source of infrared radiation 1 whose output radiation 2 is directed along a particular path. In a primary function that radiation is modulated by means of a diaphragm wheel 3 having basically two openings 4 and 5 which are separated by opaque portions so that upon rotation of the wheel 3 radiation may alternatingly pass through or be blocked from further passage. Generally speaking this is an example involving only a common practice in this field and one can use in the alternative an infrared source 1 which is turned on and off for purposes of modulation.

Figure 1:
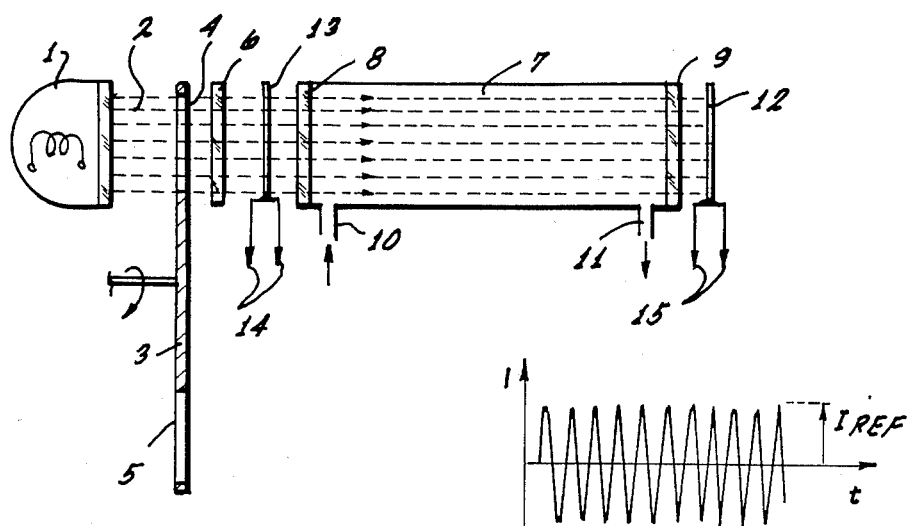
FIG. 1 illustrates a simple photometer constructed in accordance with the preferred embodiment of the present invention for practicing the best mode thereof.

The modulated radiation passes through an interference filter 6 which limits passage to certain frequencies. Basically the radiation is to pass through a cuvette or measuring chamber 7 having an entrance window 8 and exit window 9. These windows are permeable or transmissive to infrared radiation.

As the basic feature of the invention cuvette 7 is not partitioned. It is being passed through by a gas, there being an inlet 10 and outlet 11 accordingly. The gas which is forced to pass through the cuvette 7 is basically comprised of a host or carrier gas containing a certain amount of a different gas whose content is to be detected quantitatively.

Radiation leaving the cuvette 7 through the exit window 9 will reach an external or exit receiver or detector 12. This receiver is constructed as a foil or layer of polyvinylidenfluoride or PVDF. Reference numeral 15 refers to a pair of terminals or contacts between which a certain voltage is generated when infrared radiation reaches this detector 12. This voltage constitutes the measuring signal.

In accordance with the invention an input receiver is interposed between the interference filter 6 and the entrance window 8 for the cuvette. This second, input receiver 13 is likewise comprised of foil made of PVDF and has a thickness sufficient to render it partially permeable or transmissive for radiation including radiation permitted to pass through the interference filter 6. The interference filter 6 will pass only a portion of the infrared radiation 2 because the total amount available from the source 1 may be unduly heating particularly the receiver 13.

On the other hand the reduction in radiation by means of interference filter (rather than any other filter) permits here the providing of a certain selectivity with regard to the detection process. The interference filter may be attuned to particular frequency bands which are significant in some form with regard to the infrared radiation absorption characteristics of the measuring gas and/or of the host gas.

It can thus be seen that the receiver or detector 13 is passed through by the entire radiation that is permitted to pass through the filter 6. It will extract from that radiation a certain definite portion depending on the physical parameters of the receiver 13. That portion is, however, an immediate and direct indicator of the radiation that is permitted to pass into the cuvette through the entrance window 8. The radiation being absorbed by the detector 13 will generate an electrical signal that can be extracted from the terminals 14. This voltage will serve as a reference signal to be compared with the measured signal as derived from terminals 15. The pyroelectric effect is utilized by these type of detectors operating on PVDF basis.

The absorption of the PVDF receivers 12 and 13 themselves can be modified simply through painting a portion of the effective, radiation-receiving surface of either or both of the receivers 12 and 13 with a black paint or other cover. By this simple feature one may also adjust the relationship between reference and measuring signals.

Figure 2:
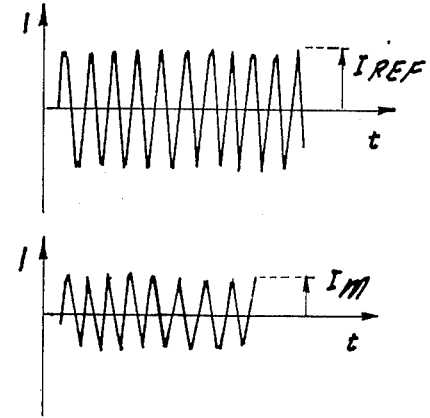
FIG. 2 illustrates in two diagrams certain signals generated by and within the photometer shown in FIG. 1.

FIG. 2 shows the signals as produced by the pyroelectric effect in the PVDF receivers. The upper diagram shows the reference signal Iref from detector 13; the lower diagram illustrates the measuring signal Im from detector 12. The oscillating characteristics of the signals results from the modulation provided by the wheel 3. The time scale is the same in both diagrams. The measuring signal Im is smaller owing to the absorption of radiation inside the cuvette 7. The two signals Im and Iref are related to each other on the basis of mathematical relationship whereby e.g. a final output signal is produced by a circuit (not shown) which realizes the relationship:

$$A1 = (Iref-Im)/Iref.$$

Figure 3:
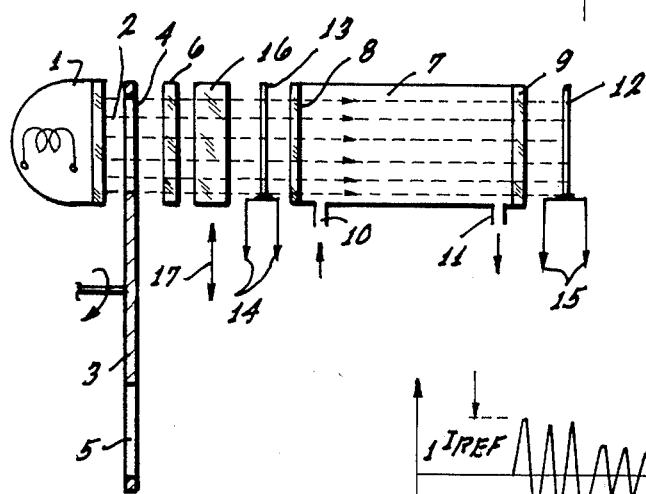
FIG. 3 illustrates a photometer that includes certain improvements over the photometer shown in FIG. 1.

FIG. 3 illustrates a modified and improved photometer having basically the same characteristics and features as well as elements as the one shown in FIG. 1, and correspondingly, similar parts in the two figures are identified by the same reference numerals. The photometer in FIG. 3 is additionally equipped with a selecting cuvette 16 being interposed between the reference and input detector 13 and the interference filter 6. This cuvette 16 is filled with the same gas whose quantitative content in the host gas is to be determined. Often the concentration of $CO_2$ within a host gas (e.g. air or automobile exhaust gas) is to be determined and in this case the cuvette 16 will be filled with a definite amount of $CO_2$, either completely or at a known quantity within the same kind of host gas. Alternatively the selecting cuvette 16 may be filled with a host gas which has, at least within the range of interest, the same absorption bands.

Figure 4:
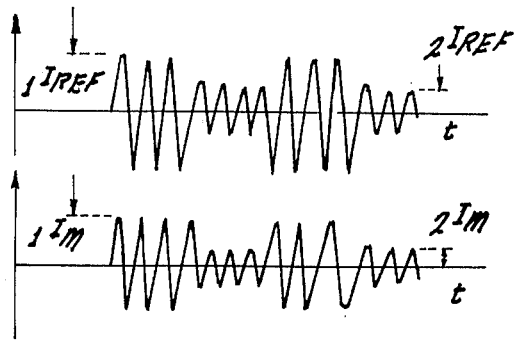
FIG. 4 illustrates certain signals as they are generated within the photometer shown in FIG. 3.

This cuvette 16 is moved back and forth, transversely to the direction of the radiation 2 and as indicated by the double arrow 17. Therefore the cuvette 16 is selectively included in or excluded from the beam 2 of radiation whereby the back and forth movement has a frequency which is lower than the modulating frequency provided by the wheel 3. As a consequence a certain additional amplitude modulation occurs in the measuring and reference signals as is shown in FIG. 4. The upper diagram shows the normal amplitude level for the reference signal Iref which occurs when the cuvette 16 is withdrawn from the radiation path, but upon insertion the amplitude of the reference signal drops the oscillatory character of amplitude waxing and waning is readily discernible in the FIG. 4. The lower diagram of that figure shows the companion modulation of the measuring signal. For purposes of measurement one is interested only in the maximum and minimum amplitude level and these are identified as 1Iref, 2Iref, 1Im and 2Im. The resulting signals are interrelated to obtain a final output signal A3 in accordance with the following mathematical relationship:

$$A_3 = \frac{(1^{I}\text{ref}/2^{I}\text{ref} - 1^{I}M/2^{I}M)}{\frac{1^{I}\text{ref}}{2^{I}\text{ref}}}$$

It was found that in such a case the signal stability is greatly enhanced and the accuracy of the photometer is greatly improved because interferences resulting from temperature variations, soiling of the cuvette or undesirable changes in the emissivity of the source 1 are to considerable extent eliminated.

The invention is not limited to the embodiments described above, but all changes and modifications thereof, not constituting departures from the spirit and scope of the invention, are intended to be included.

I claim:

1. Photometer having a means for providing modulated infrared radiation, a measuring cuvette traversed by a measuring gas, the cuvette having an entrance window facing said means for providing radiation and an exit window, there being an output detector provided at said exit window, the improvement comprising:
    a second infrared detector made of polyvinylidenfluoride, being partially transmissive to infrared radiation and being disposed between said means for providing modulated radiation and the entrance window of said cuvette.

2. Photometer in accordance with claim 1, said output detector also being made of polyvinylidenfluoride.

3. Photometer as in claim 2 at least one of the detectors having a physical extension transversely to a direction of propagation of the radiation corresponding to the entrance and/or exit windows of the cuvette.

4. Photometer as in claim 1 wherein at least one of the radiation detectors having on its side facing radiation, at least a partial layer of black coating.

5. A photometer as in claim 1 and including a selecting cuvette arranged for placement in a position between said second detector and said means for providing modulated radiation, there being means for alternatingly placing said selecting cuvette into said position or removing it therefrom.

* * * * *